US00PP28210P3

(12) United States Plant Patent
van Kleinwee

(10) Patent No.: US PP28,210 P3
(45) Date of Patent: Jul. 18, 2017

(54) *PETUNIA* PLANT NAMED 'PEHY0006'

(50) Latin Name: *Petunia hybrida*
Varietal Denomination: PEHY0006

(71) Applicant: SYNGENTA PARTICIPATIONS AG, Basel (CH)

(72) Inventor: Theodorus Cornelis van Kleinwee, Enkhuizen (NL)

(73) Assignee: Syngenta Participations AG, Basel (CH)

( * ) Notice: Subject to any disclaimer, the term of this patent is extended or adjusted under 35 U.S.C. 154(b) by 8 days.

(21) Appl. No.: 14/998,450

(22) Filed: Jan. 5, 2016

(65) Prior Publication Data

US 2016/0198608 P1 Jul. 7, 2016

Related U.S. Application Data

(60) Provisional application No. 62/099,638, filed on Jan. 5, 2015.

(51) Int. Cl.
*A01H 5/02* (2006.01)

(52) U.S. Cl.
USPC ..... Plt./356.23

(58) Field of Classification Search
USPC ..... Plt./356.1, 356.23
See application file for complete search history.

*Primary Examiner* — Susan McCormick Ewoldt
(74) *Attorney, Agent, or Firm* — Dale Skalla

(57) ABSTRACT

A new *Petunia* plant named 'PEHY0006' particularly distinguished by salmon-pink flowers, medium green foliage, excellent branching, mounding plant habit, relatively low vigour and medium sized flowers.

1 Drawing Sheet

Latin name of the genus and species of the plant claimed: *Petunia hybrida.*

Varietal denomination: 'PEHY0006'.

BACKGROUND OF THE NEW PLANT

The present invention comprises a new *Petunia*, botanically known as *Petunia hybrida*, and hereinafter referred to by the variety name 'PEHY0006'.

'PEHY0006' is a product of a planned breeding program. The new cultivar has salmon-pink flowers, medium green foliage, excellent branching, mounding plant habit, relatively low vigour and medium sized flowers.

'PEHY0006' originated from originated from a hybridization made in October 2005 in a controlled breeding environment in Enkhuizen, Netherlands. The female parent was the unpatented proprietary plant designated 'B0989-1' with salmon flower color, medium flower size, and a more upright plant habit.

The male parent of 'PEHY0006' was an unpatented proprietary plant identified as 'B1070-1' with purple rose flower color, a rather big flower, semi-trailing habit and rather late flowering The resulting seeds were sown in February 2006. 'PEHY0006' was selected as a single flowering plant within the progeny of the stated cross May 16, 2006 in a controlled environment in Enkhuizen, Netherlands.

The first act of asexual reproduction of 'PEHY0006' was accomplished when vegetative cuttings were propagated from the initial selection in June 2006 in a controlled environment in Enkhuizen, Netherlands.

BRIEF SUMMARY OF INVENTION

Horticultural examination of plants grown from cuttings of the plant initiated in September 2006 in Gilroy, Calif., USA, and continuing thereafter, has demonstrated that the combination of characteristics as herein disclosed for 'PEHY0006' are firmly fixed and are retained through successive generations of asexual reproduction.

'PEHY0006' has not been observed under all possible environmental conditions. The phenotype may vary significantly with variations in environment such as temperature, light intensity, and day length.

A Plant Breeder's Right for this cultivar has not yet been applied for. 'PEHY0006' has not been made publicly available more than one year prior to the filing of this application.

The following traits have been repeatedly observed and are determined to be basic characteristics of the new variety. The combination of these characteristics distinguishes this *Petunia* as a new and distinct variety.

BRIEF DESCRIPTION OF THE PHOTOGRAPHS

The accompanying photographic drawing shows typical flower and foliage characteristics of 'PEHY0006' with colors being as true as possible with an illustration of this type.

The photographic drawing shows in FIG. 1. a whole flowering plant of the new variety.

DETAILED BOTANICAL DESCRIPTION

The plant descriptions and measurements were taken in late September 2014, from plants grown for breeding purposes in a greenhouse in Enkhuizen, Netherlands. The plants had been planted around Jul. 10, 2014. They were approximately 11 weeks of age and growing in 19 cm containers. They had been cut back a few weeks before the observations.

The aforementioned photograph was taken in April 2012 from plants growing in a greenhouse trial in Andijk, Netherlands. The plant was approximately 12-13 weeks of age.

Color references are made to The Royal Horticultural Society Colour Chart (R.H.S.) 2001.

TABLE 1

DIFFERENCES BETWEEN THE NEW VARIETY 'PEHY0006' AND A SIMILAR VARIETY

| | PEHY0006' | 'Dueplupin', also known as 'Petunia Plus Pinkalicious' |
|---|---|---|
| Flower color: | Salmon-pink, stable | Deep pink |
| Flowering response: | Early | Late |
| Flower size: | Medium | Rather large |

Plant:

*Form, growth and habit.*—Mounding, free flowering, free branching.

*Plant height.*—13 cm.

*Plant height (inflorescence included).*—19 cm.

*Plant width.*—26 cm.

Roots:

*Number of days to initiate roots.*—About 12 days at about 22 degrees C.

*Number of days to produce a rooted cutting.*—18-24 days at 22 degrees C.

*Type.*—Fine, fibrous, free branching.

*Color.*—RHS near N155B.

Foliage:

*Arrangement of leaves.*—Simple, opposite, sometimes decussate.

*Immature leaf, color upper surface.*—RHS 144A-B.

*Immature leaf, color lower surface.*—RHS 144B-C.

*Mature leaf, color, upper surface.*—RHS 137C.

*Mature leaf, color lower surface.*—RHS 144A-B.

*Length.*—6.5 cm.

*Width.*—3 cm.

*Shape.*—Ovate.

*Base shape.*—Obtuse.

*Apex shape.*—Acute or obtuse.

*Margin.*—Entire.

*Texture, upper surface.*—Pubescent, and much hair along the edges.

*Texture, lower surface.*—Pubescent with shorter hair.

*Color of veins, upper surface.*—RHS 144B.

*Color of veins, lower surface.*—RHS 144B.

*Petiole color.*—RHS 144D.

*Length.*—0.7 cm.

*Diameter.*—0.3-0.4 cm.

*Texture.*—Pubescent.

Stem:

*Quantity of main branches per plant.*—5.

*Color of stem.*—RHS 144A-B.

*Length of stem.*—18 cm.

*Diameter.*—0.3 cm.

*Length of internodes.*—2.5-3 cm.

*Texture.*—Hirsute.

*Pedicel, color.*—RHS 144A-B.

*Length.*—3 cm.

*Diameter.*—0.2-0.3 cm.

*Texture.*—Hirsute.

Inflorescence:

*Type of inflorescence.*—Single flowers, emerging from the upper nodes of the stem.

*Blooming habit.*—Continuous flowering throughout the summer months.

*Start of flowering.*—8 weeks from planting rooted cuttings.

*Quantity of flowers per plant.*—About 15-20.

*Lastingness of individual blooms on the plant.*—Up to 14 days in greenhouse, depending on temperature.

*Fragrance.*—None.

Bud (just when opening/showing color):

*Color.*—RHS 145D at the base, RHS 75B near upper end; over the whole length are veins, RHS 145A.

*Length.*—4 cm.

*Width.*—From 0.5 cm to 1 cm at the top.

*Shape.*—Oblong.

Immature flower:

*Diameter.*—Approximately 4.5 cm.

*Color, upper surface.*—From RHS 53D near the center to RHS 55A and RHS 55B near the edges.

*Color, lower surface.*—RHS 55D.

Mature flower:

*Shape.*—Salver-shape, with funnel-shape base, formed by 5 fused petals.

*Horizontal diameter.*—5.7-6.2 cm.

*Vertical diameter.*—4 cm.

*Color, upper surface.*—Mainly RHS 52B, becoming lighter towards the margin: RHS 55B; and RHS 52A around the center and for the weak veins.

*Color, lower surface.*—RHS 55D.

*Petal apex shape.*—Weakly mucronulate.

*Petal base shape.*—Fused.

*Petal margin.*—Entire.

*Waviness of petals margin.*—Weak to medium.

*Petal lobation.*—Weak to medium.

*Petal texture, upper surface.*—Glabrous, papillose.

*Petal texture, lower surface.*—Papillose, hirsute.

*Corolla tube, color inside.*—RHS 154D.

*Corolla tube, color outside.*—RHS 145B.

*Corolla tube length.*—3 cm.

*Corolla tube, diameter.*—0.9 cm.

*Corolla tube, texture.*—Hirsute outside.

Calyx:

*Form.*—5 sepals in a whorl, fused at the base.

*Color, upper surface.*—RHS 137B.

*Color, lower surface.*—RHS 137D.

*Length.*—1.8-2 cm.

*Width.*—0.4 cm.

*Shape.*—Ensiform, fused at the base.

*Apex shape.*—Acute.

*Base.*—Fused.

*Margins.*—Entire.

*Texture, upper surface.*—Hirsute.

*Texture, lower surface.*—Hirsute with very short hair.

Reproductive organs:

Gynoecium:

*Pistil.*—1.

*Length.*—2.2 cm.

*Style color.*—RHS 145C.

*Style length.*—2.1 cm.

*Stigma color.*—RHS 145D.

*Stigma shape.*—Discoid.

*Ovary color.*—RHS 143C.

Androecium:

*Number of stamens.*—5.

*Color of filaments.*—RHS 155C.

*Length filaments.*—2-2.3 cm.

*Anther color.*—RHS 8D.

*Anther length.*—0.1-0.2 cm.

*Anther shape*.—Elliptical.

*Color of pollen*.—RHS 11C.

*Pollen amount*.—Plenty.

Fertility/seed set: Has not been observed on this hybrid.

Disease/pest resistance: Has not been observed on this hybrid.

What is claimed is:

1. A new and distinct variety of *Petunia* plant named 'PEHY0006' substantially as illustrated and described herein.

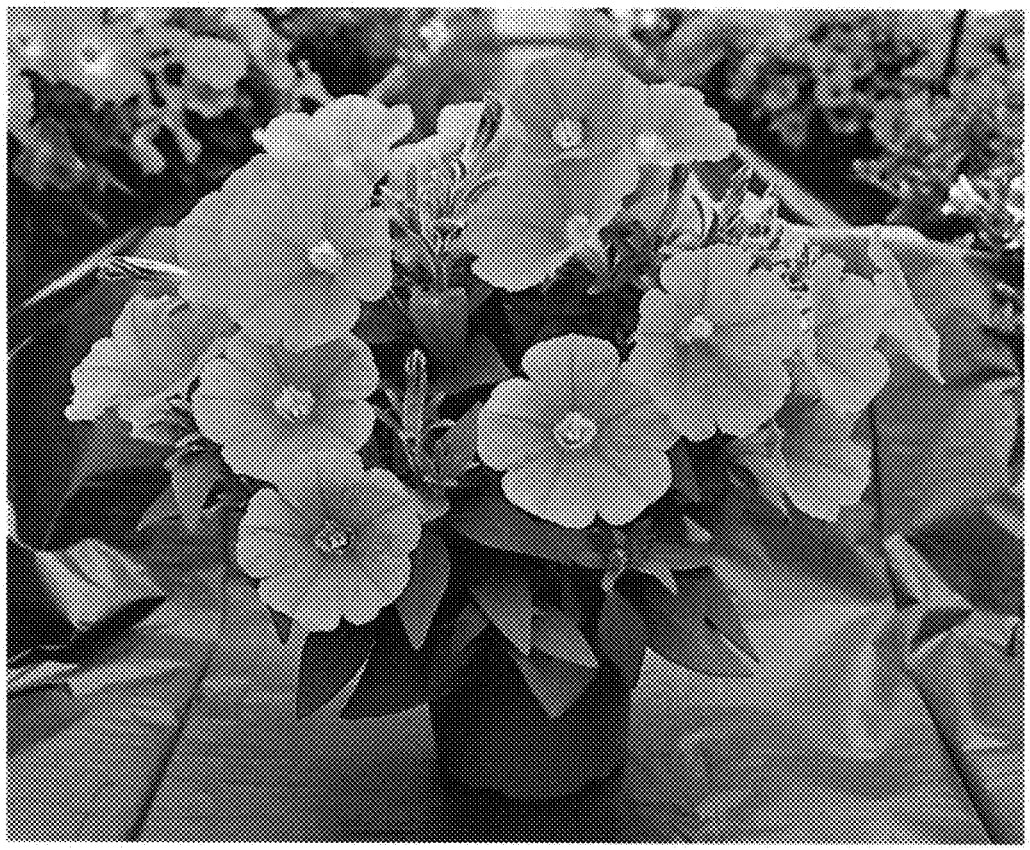

* * * * *